(12) United States Patent
Lorenz

(10) Patent No.: US 9,713,474 B2
(45) Date of Patent: Jul. 25, 2017

(54) ENDOSCOPIC STAPLER

(71) Applicant: THE CLEVELAND CLINIC FOUNDATION, Cleveland, OH (US)

(72) Inventor: Robert R. Lorenz, Shaker Heights, OH (US)

(73) Assignee: The Cleveland Clinic Foundation, Cleveland, OH (US)

( * ) Notice: Subject to any disclaimer, the term of this patent is extended or adjusted under 35 U.S.C. 154(b) by 760 days.

(21) Appl. No.: 14/028,783

(22) Filed: Sep. 17, 2013

(65) Prior Publication Data

US 2014/0076955 A1 Mar. 20, 2014

Related U.S. Application Data

(60) Provisional application No. 61/701,852, filed on Sep. 17, 2012.

(51) Int. Cl.
| | |
|---|---|
| *A61B 17/04* | (2006.01) |
| *A61B 17/08* | (2006.01) |
| *A61B 17/072* | (2006.01) |
| *A61B 17/29* | (2006.01) |

(52) U.S. Cl.
CPC ........ *A61B 17/07207* (2013.01); *A61B 17/29* (2013.01); *A61B 2017/2906* (2013.01)

(58) Field of Classification Search
CPC ... A61B 17/07207; A61B 17/04; A61B 17/08; A61B 17/072
USPC .......... 227/175.1–181.1; 606/139, 142, 153, 606/205, 147, 143, 49, 50, 51, 151, 399
See application file for complete search history.

(56) References Cited

U.S. PATENT DOCUMENTS

| | | | | |
|---|---|---|---|---|
| 4,316,468 A | * | 2/1982 | Klieman | A61B 17/128 227/145 |
| 5,290,299 A | | 3/1994 | Fain et al. | |
| 5,403,326 A | * | 4/1995 | Harrison | A61B 17/0643 128/898 |
| 5,527,319 A | * | 6/1996 | Green | A61B 17/1285 606/139 |
| 5,573,541 A | | 11/1996 | Green et al. | |

(Continued)

FOREIGN PATENT DOCUMENTS

WO 2012044643 A9 4/2012

*Primary Examiner* — Hemant M Desai
*Assistant Examiner* — Mary Hibbert
(74) *Attorney, Agent, or Firm* — Tarolli, Sundheim, Covell & Tummino LLP

(57) ABSTRACT

An endoscopic stapler comprises a first jaw and a second jaw. The first jaw includes structure for retaining a plurality of staples. The first jaw and second jaw are mounted to permit pivotal movement of the first and second jaws relative to one another. The endoscopic stapler also comprises at least one clamp member for clamping tissue and pulling the tissue into a position between the first jaw and the second jaw to facilitate inserting at least one staple of the plurality of staples into the tissue. A first handle is operably coupled with the first jaw such that movement of the first handle effects delivery of the at least one staple of the plurality of staples to the tissue. A second handle is operably coupled with the second jaw and the at least one clamp member such that movement of the second handle effects movement of the second jaw and movement of the at least one clamp member.

15 Claims, 11 Drawing Sheets

(56) References Cited

U.S. PATENT DOCUMENTS

| | | | |
|---|---|---|---|
| 5,597,107 A * | 1/1997 | Knodel | A61B 17/07207 |
| | | | 227/175.2 |
| 5,779,132 A | 7/1998 | Knodel et al. | |
| 5,871,135 A | 2/1999 | Williamson, IV et al. | |
| 7,673,781 B2 | 3/2010 | Swayze et al. | |
| 7,819,299 B2 | 10/2010 | Shelton, IV et al. | |

\* cited by examiner

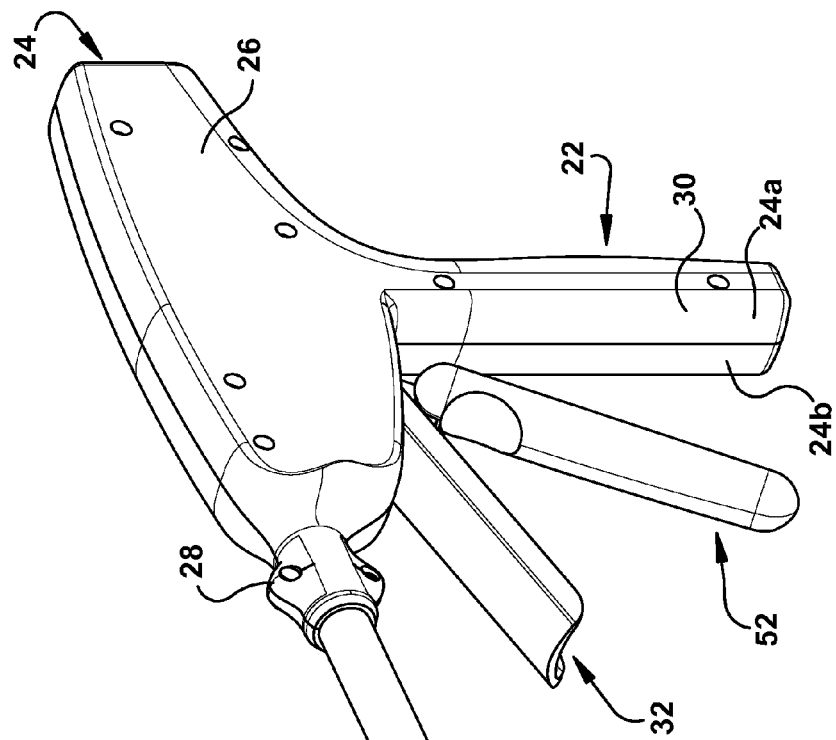
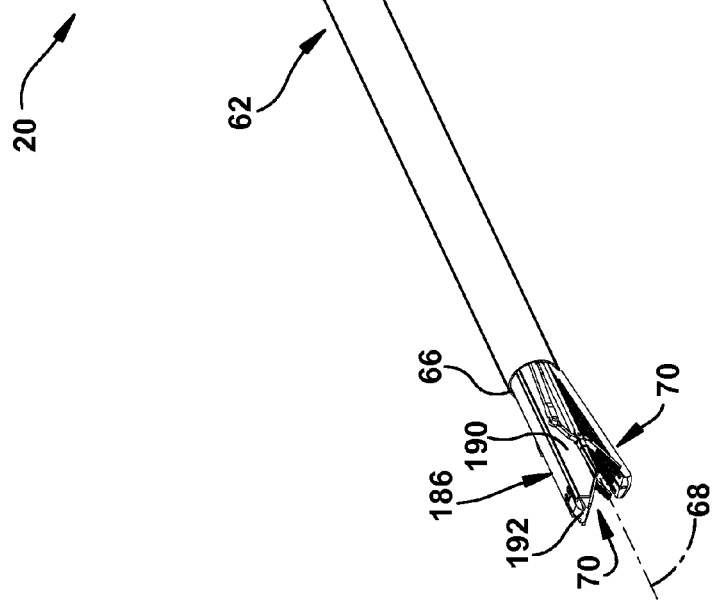
Fig. 1

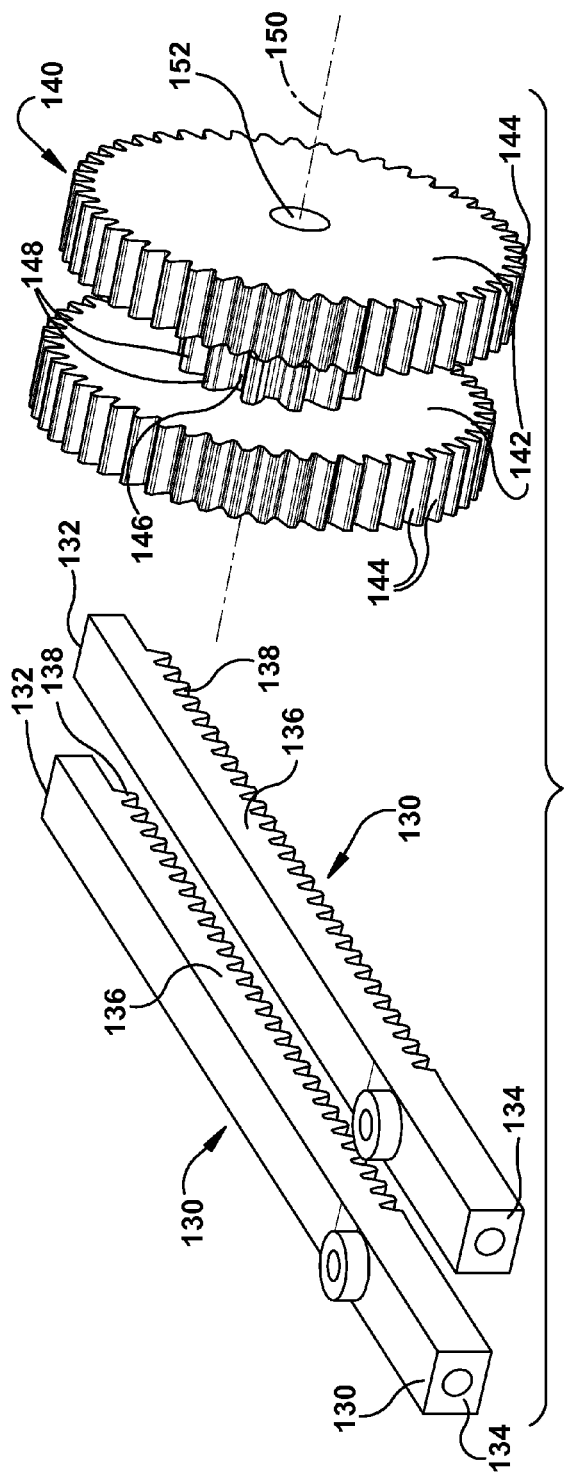
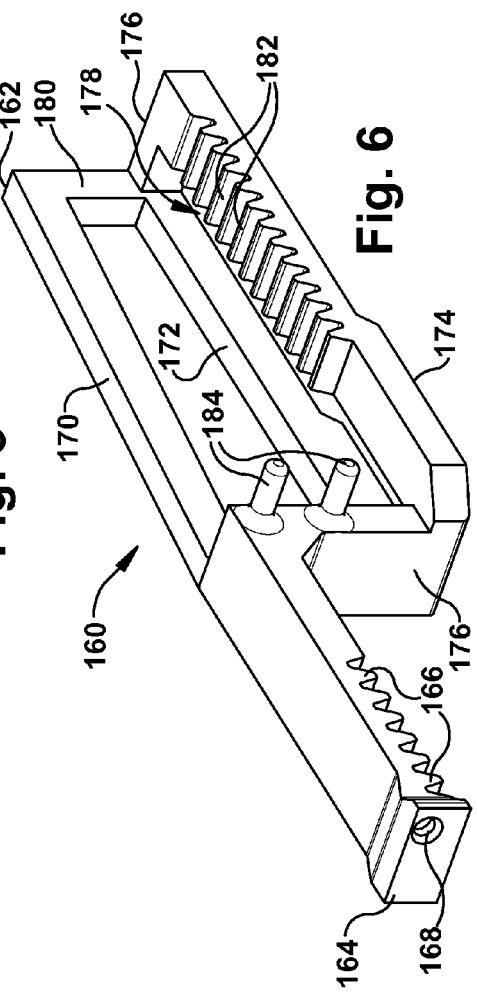
Fig. 5
Fig. 6

ENDOSCOPIC STAPLER

CROSS-REFERENCE TO RELATED APPLICATION

This application claims the benefit of U.S. Provisional Patent Application No. 61/701,852 filed on Sep. 17, 2012, and entitled ENDOSCOPIC STAPLER, which is incorporated herein by reference in its entirety.

TECHNICAL FIELD

The present invention relates to an endoscopic stapler and, in particular, relates to a stapler that clamps and pulls tissue before stapling the tissue.

BACKGROUND OF THE INVENTION

Tissue stapling is used in a variety of clinical applications to treat injury, correct deformities, and promote healing. One application that requires tissue stapling is Zenker's Diverticulum (ZD). ZD is a condition in which excessive pressure within the lower pharynx causes the weakest portion of the pharyngeal wall to balloon out, forming a diverticulum which may reach several centimeters in diameter. Symptomatic cases of ZD have been traditionally treated by neck surgery to either resect the diverticulum and/or incise the cricopharyngeus muscle. However, in recent times non-surgical endoscopic techniques have gained more importance as they allow for much faster recovery, and the currently preferred treatment is endoscopic stapling, i.e. opening up the diverticulum via a stapler inserted through a tube in the mouth, which may be performed through a transoral endoscope.

In performing endoscopic treatment of ZD, it is important that enough of the pharyngeal wall be stapled to reduce the likelihood of recividism and continued dysphagia. Due to the limited field of view, obtaining purchase on the sac wall is technically challenging, but is essential for adequate correction of the deformity. Accordingly, it is desirable to provide an endoscopic stapling device that ensures adequate purchase of the pharyngeal wall during stapling.

SUMMARY OF THE INVENTION

The present invention is directed to an endoscopic stapler and, in particular, relates to a stapler that clamps and pulls tissue before stapling the tissue.

In accordance with an embodiment of the present invention, an endoscopic stapler comprises a first jaw and a second jaw. The first jaw includes structure for retaining a plurality of staples. The first jaw and second jaw are mounted to permit pivotal movement of the first and second jaws relative to one another. The endoscopic stapler also comprises at least one clamp member for clamping tissue and pulling the tissue into a position between the first jaw and the second jaw to facilitate inserting at least one staple of the plurality of staples into the tissue. A first handle is operably coupled with the first jaw such that movement of the first handle effects delivery of the at least one staple of the plurality of staples to the tissue. A second handle is operably coupled with the second jaw and the at least one clamp member such that movement of the second handle effects movement of the second jaw and movement of the at least one clamp member.

In accordance with another embodiment of the present invention, an endoscopic stapler for suturing tissue comprises a first jaw and a second jaw. The first jaw includes structure for retaining a plurality of staples. The first jaw and second jaw are mounted to permit pivotal movement of the first and second jaws relative to one another. The endoscopic stapler also comprises two clamp members for clamping tissue and pulling the tissue into a position between the first jaw and the second jaw to facilitate inserting at least one staple of the plurality of staples into the tissue. The two clamp members are laterally spaced from one another. The first jaw and the second jaw are disposed laterally between the two clamp members. A handle is operably connected with the second jaw and with the clamp members such that movement of the handle effects pivotal movement of the second jaw relative to the first jaw and also effects clamping movement of the clamp members.

In accordance with a further embodiment of the present invention, a method of stapling tissue uses an endoscopic stapler. The endoscopic stapler comprises (a) a first jaw, (b) a second jaw, (c) at least one clamp member, (d) a first handle, and (e) a second handle. The first jaw includes structure for retaining a plurality of staples. The first jaw and the second jaw are mounted to permit pivotal movement of the first and second jaws relative to one another. The at least one clamp member is operable for clamping tissue and pulling the tissue into a position between the first jaw and the second jaw to facilitate inserting at least one staple of the plurality of staples into the tissue. The first handle is operably coupled with the first jaw such that movement of the first handle effects delivery of the at least one staple of the plurality of staples to the tissue. The second handle is operably coupled with the second jaw and the at least one clamp member such that movement of the second handle effects movement of the second jaw and movement of the at least one clamp member. The method comprises the step of moving the second handle to (i) actuate the at least one clamp member to clamp the tissue and pull the tissue into a position between the first and second jaws and (ii) pivot the second jaw relative to the first jaw to clamp the tissue between the first jaw and the second jaw. The method also comprises the step of moving the first handle to insert the at least one staple of the plurality of staples into the tissue while the tissue is disposed between the first and second jaws.

BRIEF DESCRIPTION OF THE DRAWINGS

The foregoing and other features and advantages of the present invention will become apparent to those skilled in the art to which the present invention relates upon reading the following description with reference to the accompanying drawings, in which:

FIG. 1 is a schematic illustration of an endoscopic stapler in accordance with an embodiment of the present invention;

FIG. 5 is a schematic illustration of a rack and a gear of the stapler of FIG. 1;

FIG. 6 is a schematic illustration of a handle rack of the stapler of FIG. 1;

DETAILED DESCRIPTION

Figure 2:
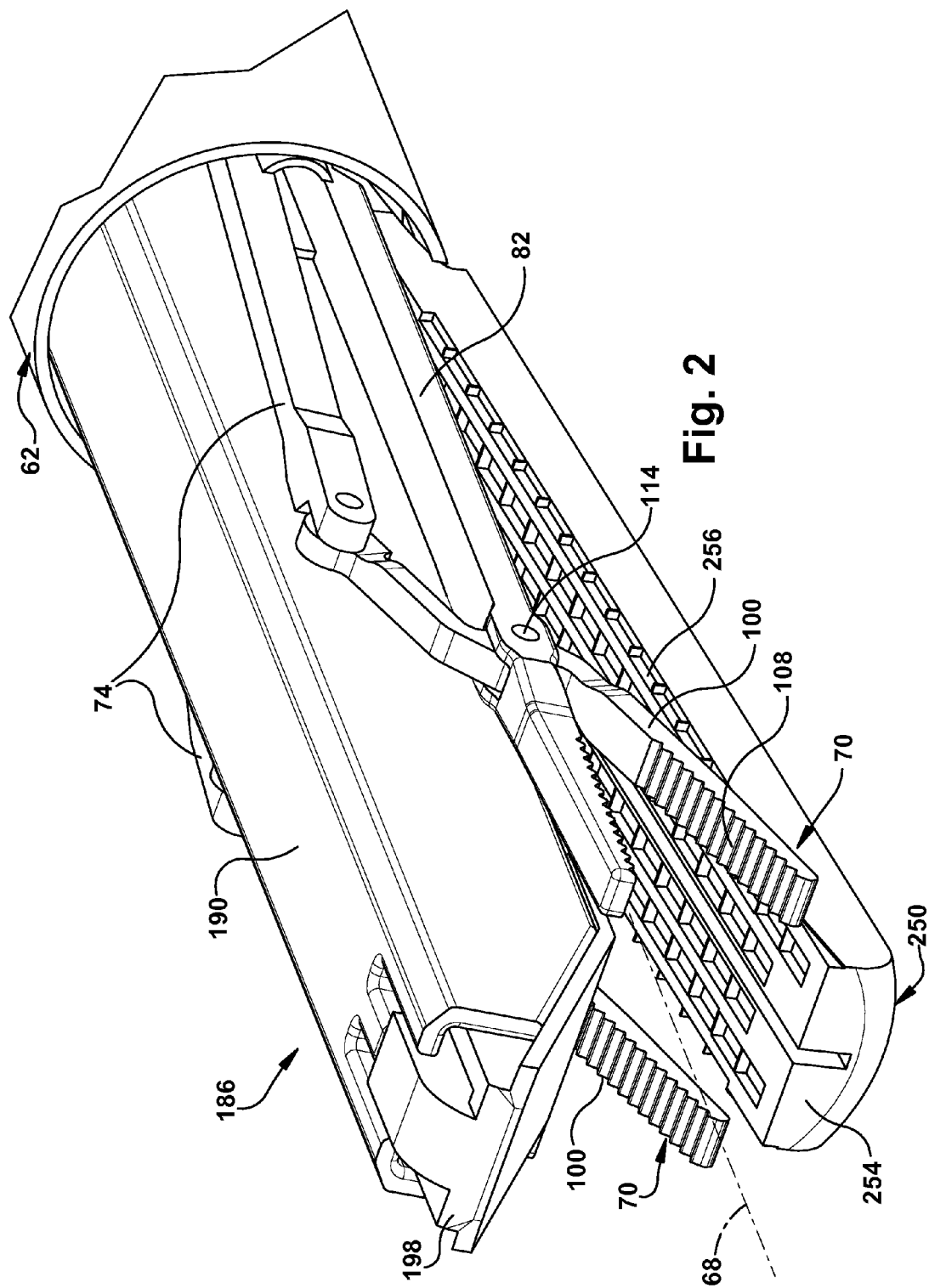
FIG. 2 is enlarged view of a portion of the stapler of FIG. 1.

The present invention relates to an endoscopic stapler and, in particular, relates to a stapler that pulls tissue inward before stapling. FIGS. 1-10 illustrate a stapling device 20 in accordance with the present invention. The stapling device 20 includes a grip assembly 22, a pair of laterally spaced-apart clamp members 70, and a stapler 186 positioned laterally between the clamp members.

The grip assembly 22 includes a housing 24, a first handle 32, a second handle 52, and a tubular member 62. As can be seen in FIG. 1, for example, the housing 24 is shaped like a pistol with an enlarged body portion 26, a tubular barrel portion 28, and a grip portion 30. The tubular barrel portion 28 projects to the left, as viewed in FIG. 1, from one end of the body portion 26. The grip portion 30 projects downwardly, as viewed in FIG. 1, from the body portion 26 at an intermediate position along the length of the body portion. The housing 24 is formed in two halves 24a and 24b that, in terms of their outer contours, are mirror images of each other.

Figure 10:
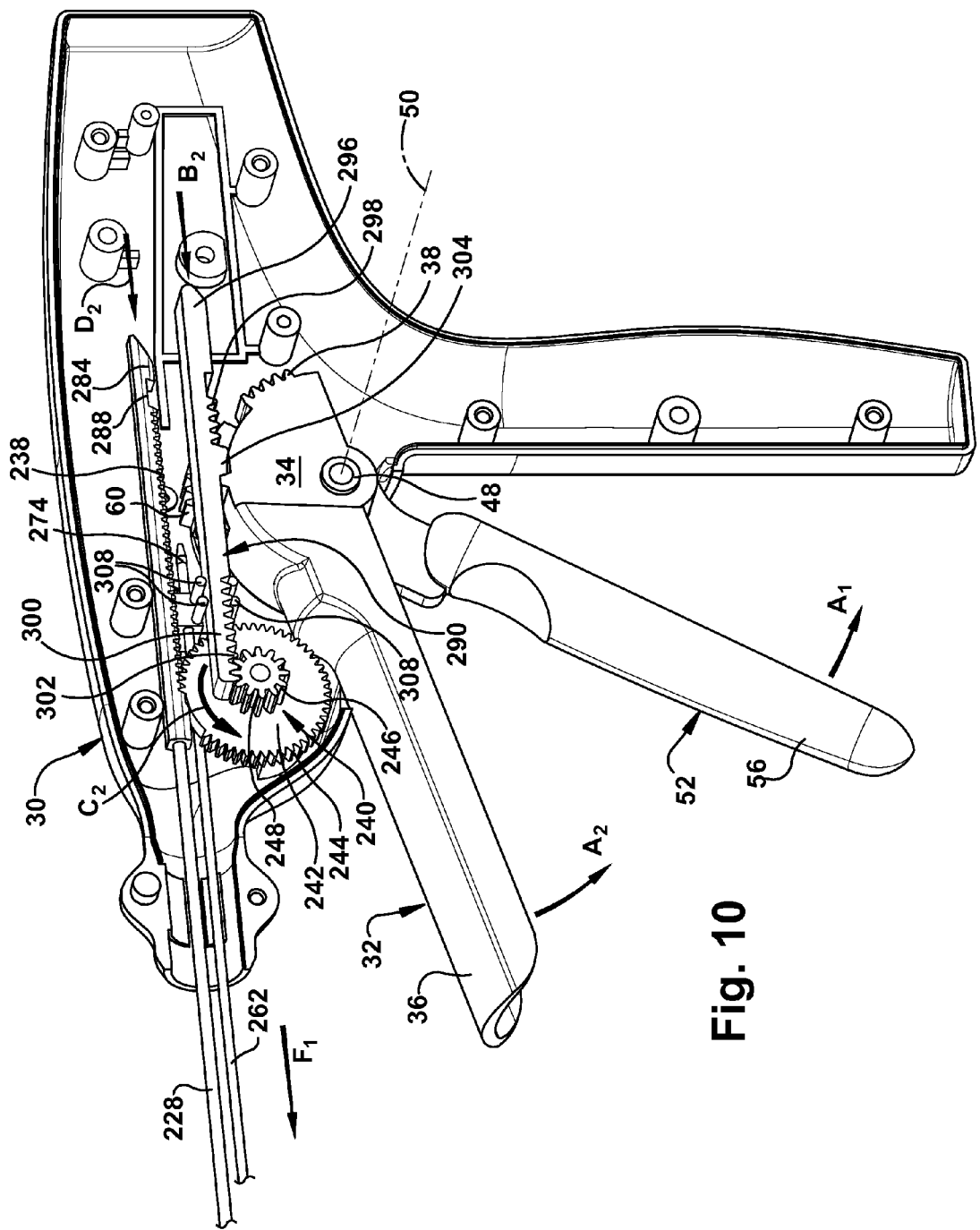
FIG. 10 is a schematic illustration of a portion of the stapler of FIG. 1.

As best seen in FIG. 10, the first handle 32 has a first end portion 34 and a second end portion 36. The first handle 32 is pivotally mounted in the body portion 26 of the housing 24 adjacent the upper end of the grip portion 30 of the housing. More particularly, the first end portion 34 of the first handle 32 is mounted on a stub shaft 48 that projects laterally from one half 24b of the housing 24. The first handle 32 is thus mounted for pivotal movement about an axis 50 that is the central longitudinal axis of the stub shaft 48. The second end portion 36 of the first handle 32 is configured to be grasped by a surgeon or other operator of the stapling device 20. The first handle 32 may be made of plastic (a polymer), metal, or other suitable biocompatible material.

Figure 4:
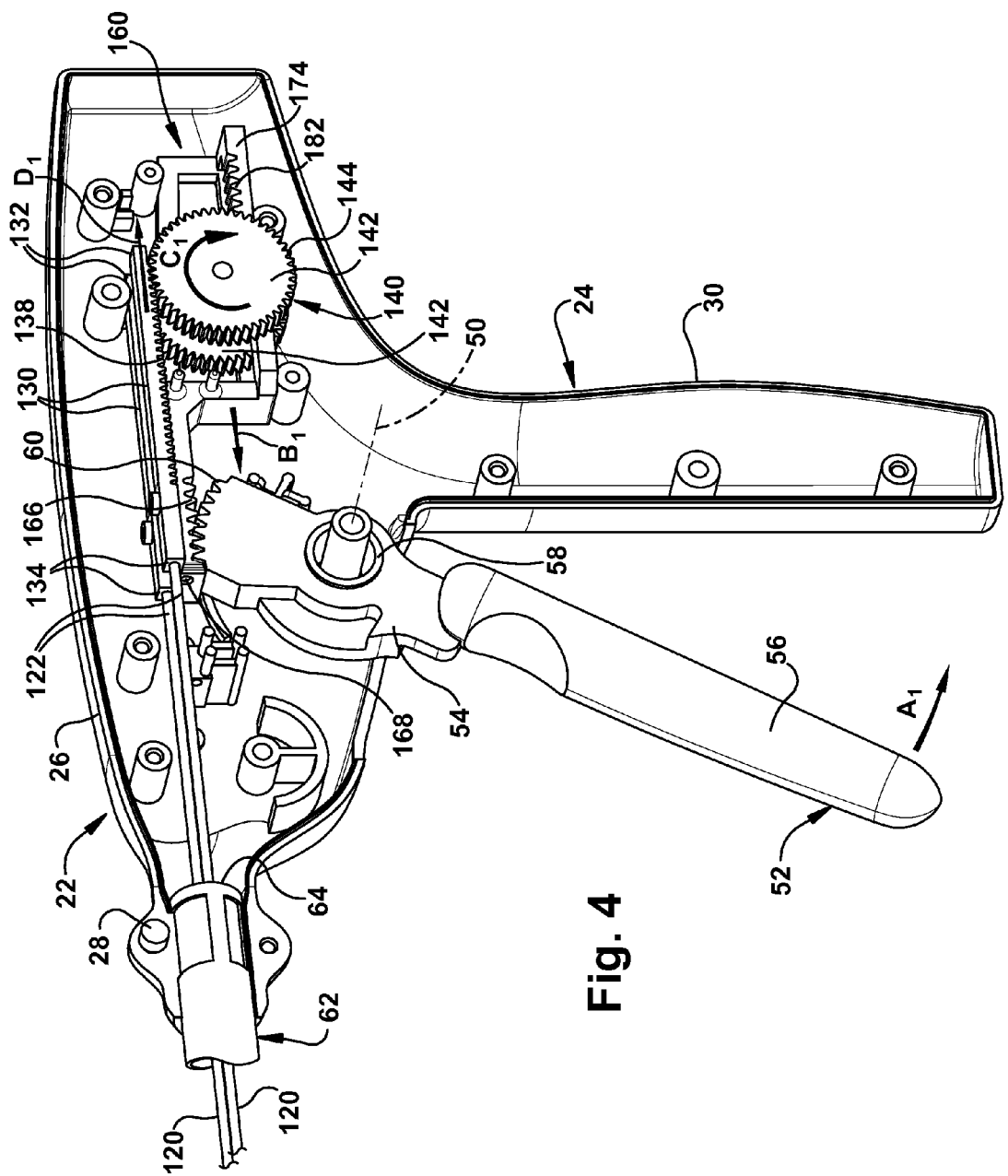
FIG. 4 is a sectional view of a portion of the stapler of FIG. 1.

The second handle 52 also has a first end portion 54 and a second end portion 56. The second handle 52 is also pivotally mounted in the body portion 26 of the housing 24 adjacent the upper end of the grip portion 30 of the housing. As best seen in FIG. 4, the first end portion 54 of the second handle 52 is mounted on a stub shaft 58 that projects laterally from one half 24b of the housing 24. The stub shaft 58 is coaxial with the stub shaft 48, but is larger in diameter and shorter in length than the stub shaft 48. The second handle 52 is thus mounted for pivotal movement about the axis 50 that is the central longitudinal axis of the stub shaft 48 and the stub shaft 58. The second end portion 56 of the second handle 52 is configured to be grasped by a surgeon or other operator of the stapling device 20. The second handle 52 may be made of plastic (a polymer), metal, or other suitable biocompatible material.

The tubular member 62 is attached to the housing 24. Specifically, the tubular member 62 has a first end 64 that is received and secured in the barrel portion 28 of the housing 24. The tubular member 62 also has a second end 66 that is spaced apart from the first end 64 and from the housing 24. The tubular member 62 thus extends away from the housing 24 along a longitudinal axis 68 from the first end 64 to the second end 66. In section taken radially or perpendicular to the longitudinal axis 68, the illustrated tubular member 62 has a circular shape, but the tubular member may have alternative shapes in radial section. The tubular member 62 surrounds at least a portion of the pair of clamp members 70 and the stapler 186. The tubular member 62 may be made of plastic (a polymer), metal, or other suitable biocompatible material.

Figure 3:
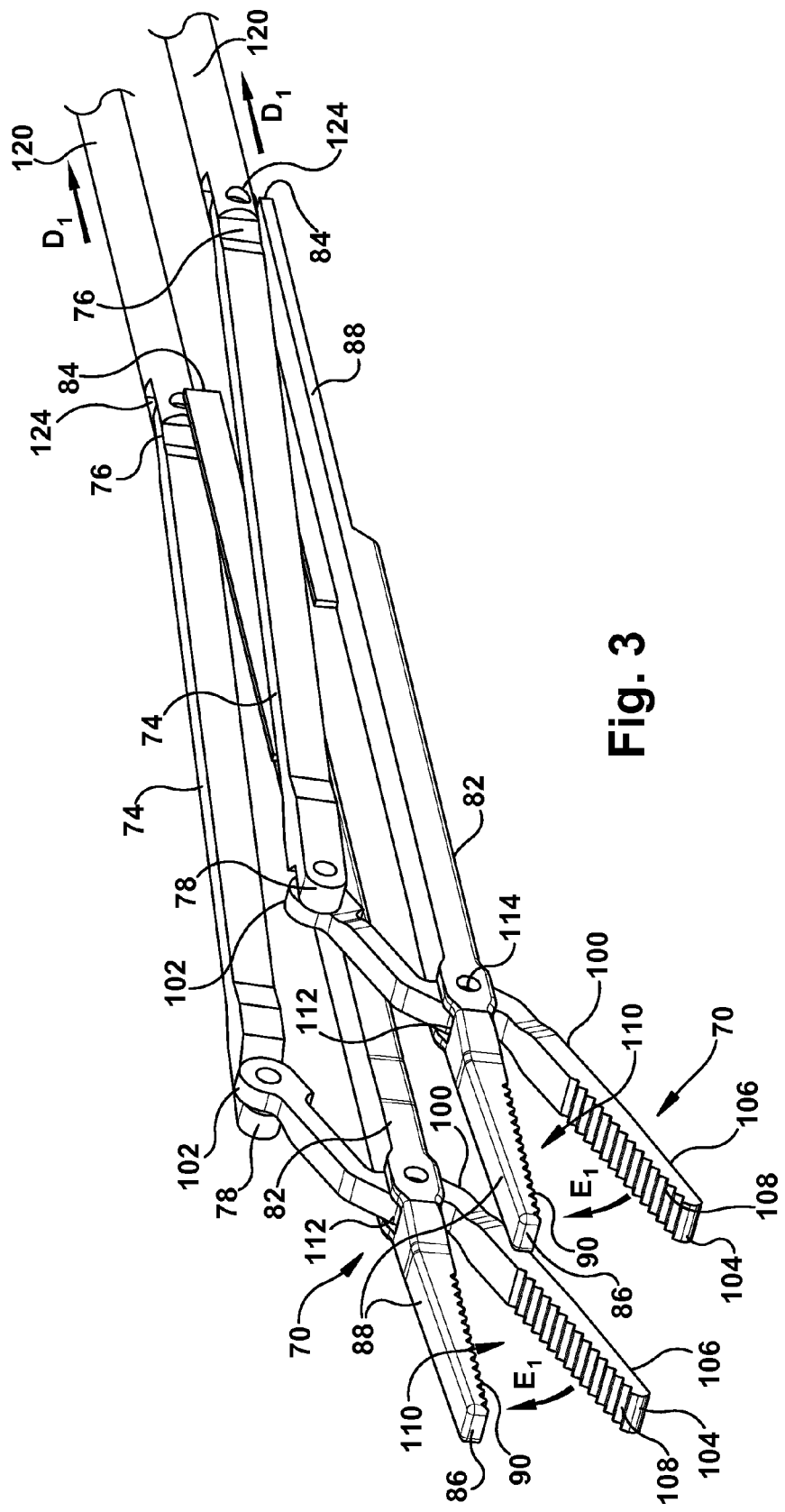
FIG. 3 is a schematic illustration of clamp members of the stapler of FIG. 1.

As shown in FIGS. 2 and 3, each of the clamp members 70 includes a first link 74, a second link 82, and a third link 100 that are interconnected. The first link 74 has a first end 76 and a second end 78. The second link 82 has a first end 84 and a second end 86. Adjacent the second end 86, a second end portion 88 of the second link 82 includes a plurality of teeth 90. The teeth 90 may be rounded, square, or frustoconical or may otherwise have an atraumatic contour. The third link 100 has a first end 102 and a second end 104. Adjacent the second end 104, a second end portion 106 of the third link 100 includes a plurality of teeth 108. The teeth 108 may be rounded, square, or frustoconical or may otherwise have an atraumatic contour. The teeth 90 on the second link 82 extend toward and face the teeth 108 on the corresponding third link 100. Together, the teeth 90 on each second link 82 and the teeth 108 on the corresponding third link 100 define a space 110 for receiving tissue.

In each clamp member 70, the third link 100 extends through an opening 112 in the second link 82. The first end 102 of the third link 100 is pivotally connected to the second end 78 of the first link 74. The third link 100 is also pivotally connected to the second link 82 at the point 114 where the third link extends through the opening 112. The pivot point 114 is intermediate the first and second ends 84 and 86, respectively, of the second link 82 and intermediate the first and second ends 102 and 104, respectively, of the third link 100. In this configuration, the second end 104 of the third link 100 is pivotable upward, as viewed in FIG. 3, toward the second end 86 of the second link 82. During pivotal movement of the third link 100, the first end 76 of the first link 74 slides along the second end portion 88 of the second link 82. The first link 74, the second link 82, and the third link 100 may be formed from plastic (a polymer), metal, or other suitable biocompatible material.

The first end 76 of the first link 74 in each clamp member 70 is secured to a corresponding clamp connecting rod 120. As shown in FIGS. 3 and 4, each of the two clamp connecting rods 120 has a first end 122 and a second end 124. The second end 124 of the clamp connecting rod 120 is secured to the first end 76 of the corresponding first link 74. Adjacent its first end 122, each clamp connecting rod 120 extends through an opening provided by the barrel portion 28 of the housing 24 and into the interior of the housing. The first end 122 of each clamp connecting rod 120 is secured to a corresponding rack 130. As best seen in FIG. 5, each of the two racks 130 has a first end 132 and a second end 134. The second end 134 of each rack 130 is secured to a corresponding clamp connecting rod 120. A portion 136 of each rack 130 intermediate the first and second ends 132 and 134 of the rack 130 includes a plurality of teeth 138 that are configured to engage and mate with a pinion gear assembly 140 rotatably mounted in the housing 24.

The pinion gear assembly 140 includes a pair of laterally spaced apart first pinion gears 142 and a second pinion gear 146 positioned between and secured for joint rotation movement with the first pinion gears. Each first pinion gear 142 has a circular shape and includes a plurality of teeth 144 that extend all around the periphery of the first pinion gear. The second pinion gear 146 also has a circular shape and includes a plurality of teeth 148 that extend all around the periphery of the second pinion gear. Each first pinion gear 142 has a first diameter and the second pinion gear 146 has a second diameter that is smaller than the first diameter. The first pinion gears 142 and the second pinion gear 146 are aligned with one another so as to be rotatable about a common axis 150. An opening 152 extends entirely through the pinion gear assembly 140. A portion (not shown) of the housing 24 projects into the opening 152 to mount the pinion gear assembly 140 on the housing and to provide a fixed axis of rotation for the pinion gear assembly relative to the housing and about the axis 150. The teeth 144 of the two first pinion gears 142 engage the teeth 138 on the portions 136 of the two racks 130. Together, the two racks 130 and the two first pinion gears 142 constitute two rack and pinion assemblies.

As can be seen in FIG. 4, the stapling device 20 further includes a handle rack 160 that is located adjacent the pinion gear assembly 140. The handle rack 160, which is best shown in FIG. 6, has a first end 162 and a second end 164. The handle rack 160 includes a first arm 170 that extends from the first end 162 of the handle rack to the second end 164. Located below the first arm 170, as viewed in FIG. 6, are a second arm 172 and a third arm 174. The second arm 172 and the third arm 174 are parallel to each other and are spaced laterally from each other and vertically from the first arm 170. The second arm 172 and the third arm 174 of the handle rack 160 extend from the first end 162 of the handle rack partway toward the second end 164. Connecting portions 176 connect opposite ends of the third arm 174 to corresponding ends of the second arm 172. The second and third arms 172 and 174 and the connecting portions 176 together define an opening 178 between the second and third arms. One of the connecting portions 176 also extends upward to connect an end of the second arm 172 to an intermediate portion of the first arm 170. A vertical strut 180 connects the other end of the second arm 172 to an end of the first arm 170 at the first end 162 of the handle rack 160.

Adjacent the second end 164 of the handle rack 160, the first arm 170 includes a plurality of teeth 166 that are presented in a downward direction, as viewed in FIG. 6. At the second end 164 of the handle rack 160, the first arm 170 includes a recess 168 presented in a direction away from the handle rack. The third arm 174 of the handle rack includes a plurality of teeth 182 that are presented in an upward direction, as viewed in FIG. 6, and that are configured to mate with the teeth 148 on the second pinion gear 146 of the pinion gear assembly 140. The handle rack 160 further includes one or more guide members 184 that extend laterally away from the connecting portion 176 that joins the second arm 172 of the handle rack to the first arm 170.

The handle rack 160 and the pinion gear assembly 140 are positioned relative to one another within the housing 24 such that the teeth 148 on the second pinion gear 146 engage the teeth 182 on the third arm 174 of the handle rack. In this arrangement, the pinion gear assembly 140 straddles the third arm 174 of the handle rack 160 such that one of the first pinion gears 142 is positioned within the opening 178 between the second arm 172 and the third arm 174 of the handle rack. The teeth 148 on the second pinion gear 146 of the pinion gear assembly 140 engage the teeth 182 on the third arm 174 of the handle rack 160 such that axial movement of the handle rack relative to the housing 24 causes rotation of the pinion gear assembly about the axis 150. Specifically, axial movement of the handle rack 160 to the left, as viewed in FIG. 4, in the direction $B_1$, causes rotation of the pinion gear assembly 140 in a clockwise direction $C_1$. Similarly, axial movement of the handle rack 160 to the right, as viewed in FIG. 4, in a direction opposite the direction $B_1$, causes rotation of the pinion gear assembly 140 in a counter-clockwise direction opposite the direction $C_1$. There is no axial movement of the pinion gear assembly 140 because the pinion gear assembly is fixed relative to the housing 24. Together, the third arm 174 of the handle rack 160 and the second pinion gear 146 constitute a rack and pinion assembly.

The handle rack 160 is also positioned within the housing 24 such that the teeth 166 on the first arm 170 of the handle rack are engaged with teeth 60 formed on the first end portion 54 of the second handle 52. The teeth 60 and the first end portion 54 of the second handle 52 are formed as a sector gear. The teeth 166 on the handle rack 160 and the teeth 60 on the first end portion 54 of the second handle 52 are configured such that pivotal movement of the second handle about the axis 50 causes axial movement of the handle rack relative to the housing 24.

FIG. 4 illustrates that the racks 130 on the clamp connecting rods 120 are aligned with the first pinion gears 142 of the pinion gear assembly 140 such that the teeth 138 on each rack engage the teeth 144 on each first pinion gear, respectively. The housing 24 may include one or more projections 44 (see FIG. 11) to help control or limit vertical movement of the handle rack 160 and thereby maintain the handle rack in toothed engagement with the second pinion gear 146 of the pinion gear assembly 140. The teeth 138 on the racks 130 and the teeth 144 on the first pinion gears 142 are configured and arranged relative to each other such that counter-clockwise rotational movement of the first pinion gears 142 causes axial movement of the racks 130 to the left, as viewed in FIG. 4. Together, the clamp connecting rods 120, the racks 130, pinion gear assembly 140, and handle rack 160 comprise a clamp linkage that operably couples the second handle 52 and the clamp members 70. In other words, the clamp connecting rods 120, the racks 130, the pinion gear assembly 140, and the handle rack 160 together provide a mechanical pathway to transmit movement of the second handle 52 to the clamp members 70 such that movement of the second handle 52 effects or produces clamping and pulling movement of the clamp members 70, as explained in more detail below.

Figure 7:
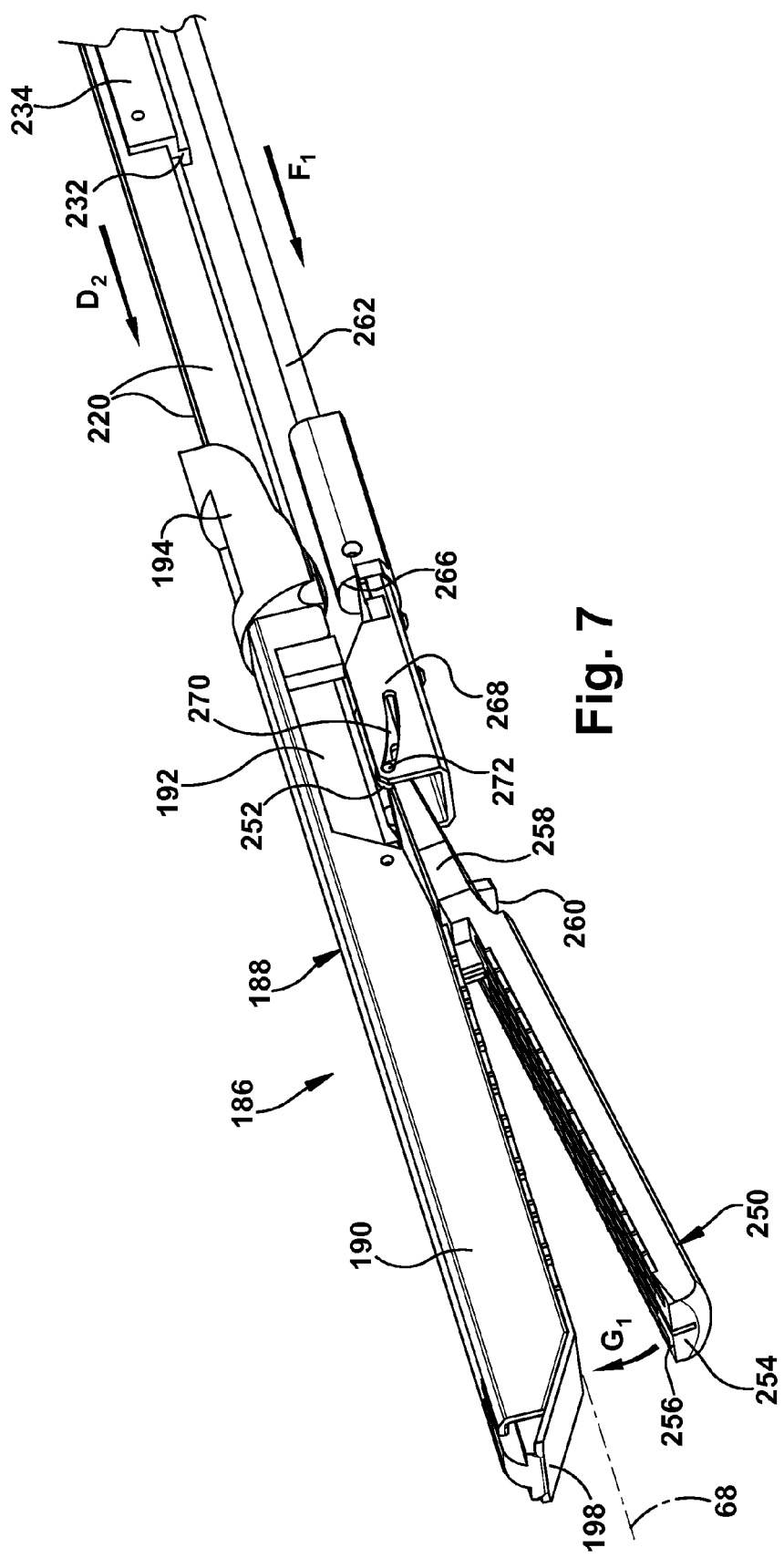
FIG. 7 is a schematic illustration of an end portion of the stapler of FIG. 1.
Figure 8:
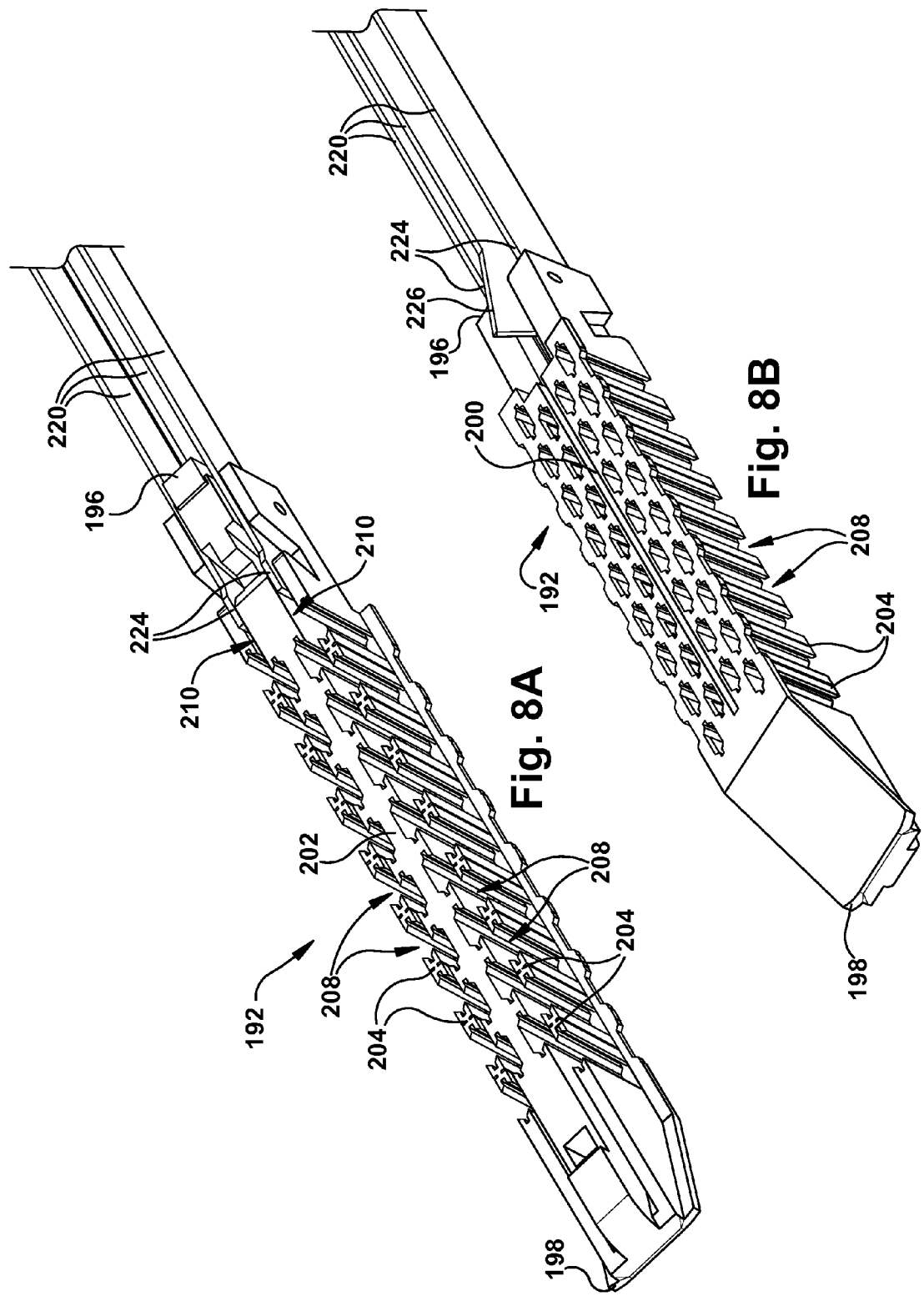
FIG. 8A is a top view of a staple cartridge of the stapler of FIG. 1.
FIG. 8B is a bottom view of the staple cartridge of FIG. 8A.

As shown in FIGS. 2 and 7, the stapler 186 includes a first jaw 188 and a second jaw 250 that is pivotable relative to the first jaw. Collectively, the first jaw 188 and the second jaw 250 resemble an alligator jaw or have an alligator jaw configuration.

The first jaw 188 comprises a cartridge holder 190 and a replaceable staple cartridge 192. The cartridge holder 190 is secured at one end to an elongated retainer 194, which, in turn, is secured to the tubular member 62. As best seen in FIGS. 8A and 8B, the staple cartridge 192 has an elongated, generally rectangular shape with a first end 196 and a second end 198. Viewed from below in FIG. 8B, the staple cartridge 192 has a configuration with a central slot 200 that extends from the first end 196 of the staple cartridge toward the second end 198 of the staple cartridge. On each side of the central slot 200 is an arrangement of solid material and openings that resembles a honeycomb. Viewed from above in FIG. 8A, the staple cartridge 192 includes a solid, axially extending central portion 202. The honeycomb-like structure that is visible from below is broken up such that a row of projections 204 extends along each side of the central portion 202. The projections 204 define openings 208 on each side of the central portion 202, which are configured to accommodate one or more rows of staples (not shown) for suturing tissue. In cases where multiple rows of staples are provided, the first and second jaws 188 and 250 of the stapler 186 may be more compact and streamlined, thereby increasing visibility in endoscopic procedures. The projections 204 and the openings 208 are covered by the staple cartridge 192. The cartridge holder 190 and the staple cartridge 192 are both made of plastic (a polymer), metal, or other suitable biocompatible material.

Figure 9:
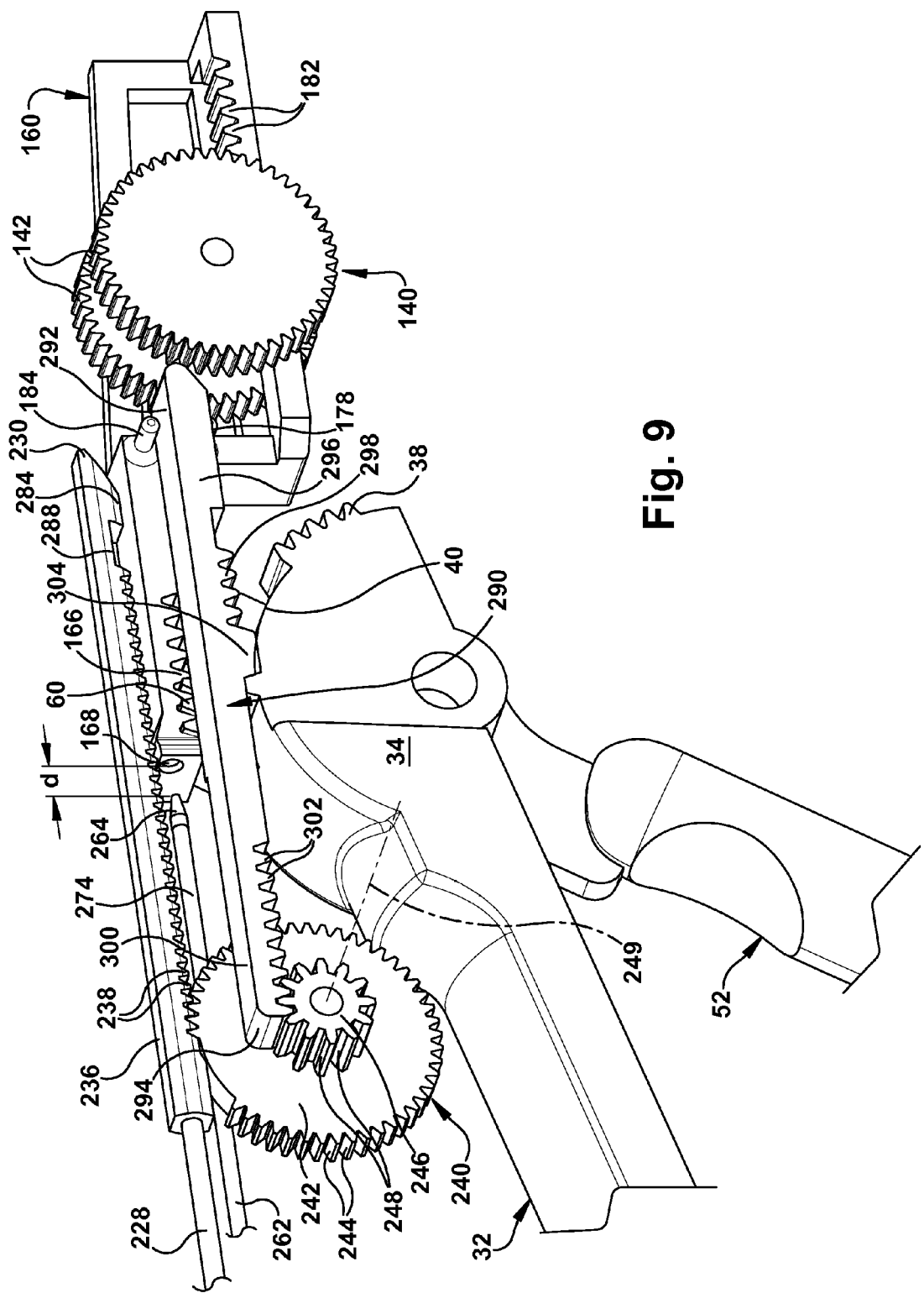
FIG. 9 is a schematic illustration of a portion of the stapler of FIG. 1.

A plurality of channels 210 extend axially through the staple cartridge 192, as viewed from above in FIG. 8A, from the first end 196 toward the second end 198. Each channel 210 receives a second end 224 of a corresponding first stapler connecting rod 220 that is movable within and relative to its corresponding channel 210. A second end 224 of an optional first stapler connecting rod 220 includes a sharpened projection 226 (FIG. 8B) and is received and movable within the central slot 200. The first ends (not shown) of all of the first stapler connecting rods 220 are attached to a second stapler connecting rod 228. As shown in FIGS. 7 and 9, the second stapler connecting rod 228 has a first end 230 received in the grip assembly 22 and an opposite second end 232 disposed adjacent the first stapler connecting rods 220. A second end portion 234 of the second stapler connecting rod 228 adjacent the second end 232 of the second connecting rod is formed with three slots (only one of which is shown in FIG. 7) to receive and hold the first stapler connecting rods 220. When the second ends 224 of the first stapler connecting rods 220 move through the channels 210 in the staple cartridge 192 to the left, as viewed in FIG. 8A, the second ends 224 contact and push on corresponding staple deployment members (not shown). As the staple deployment members (not shown) are moved to the left, as viewed in FIG. 8A, the staple deployment members engage individual staples and deploy or force the staples downward out of the staple cartridge 192 toward the second jaw 250.

The second jaw 250 has a first end 252 and a second end 254. The second jaw 250 has an elongated, generally rectangular shape similar to the shape of the first jaw 188. The second jaw 250 also extends in the same direction as the first jaw 188. The second jaw 250 includes structure 256 for bending and securing staples stored within the staple cartridge 192 of the first jaw 188. As shown in FIG. 7, a first end portion 258 of the second jaw 250 adjacent the first end 252 includes a downwardly projecting tab 260 that is received in an opening (not shown) formed in the tubular member 62 adjacent the second end 66 of the tubular member. The tab 260 helps to retain the second jaw 250 in the tubular member 62.

The first end portion 258 of the second jaw 250 is also pivotally connected to a pushrod 262. The pushrod 262 has a first end 264 and a second end 266. The second end 266 of the pushrod 262 is attached to a clip or bracket 268 that is U-shaped in section taken radially of the length of the pushrod. The legs of the U shaped bracket 268 include arcuate slots 270 that receive pins 272 projecting from both sides of the first end portion 258 of the second jaw 250. The pins 272 are slidable axially and rotatable within the slots 270 such that second jaw 250 is pivotable relative to bracket 268 and the pushrod 262. Specifically, due to the connection between the tab 260 and the tubular member 62, which holds the second jaw 250 against axial movement relative to the tubular member, relative axial movement between the pins 272 and the bracket 268, which occurs as the pushrod 262 is moved axially relative to the tubular member, causes the pins to slide in the slots 270 and simultaneously produce pivotal movement of the second jaw as a result of the arcuate shape of the slots. The second jaw 250 is thereby pivotable relative to the first jaw 188 in the direction indicated by arrow $G_1$ in FIG. 7.

As shown in FIGS. 9-10, the first end portion 274 of the pushrod 262 adjacent first end 264 of the pushrod extends into the housing 24. The first end 264 of the pushrod 262 is tapered and rounded. The rounded first end 264 is axially aligned with the recess 168 in the second end 164 of the handle rack 160. The rounded first end 264 of the pushrod 262 is dimensioned and configured to be received within the recess 168 in the second end 164 of the handle rack 160. When the handle rack 160 is positioned as far as it can move to the right, as viewed in FIG. 9, the rounded first end 264 of the pushrod 262 is spaced from the second end 164 of the handle rack and from the recess 168 by a predetermined distance indicated by "d" in FIG. 9. As the handle rack 160 moves to the left, as viewed in FIG. 9, the rounded first end 264 of the pushrod 262 enters the recess 168 and contacts the second end 164 of the handle rack. Thereafter, as the handle rack 160 continues to move to the left, as viewed in FIG. 9, the handle rack pushes the pushrod 262 to the left, as viewed in FIG. 9. The handle rack 160 and the pushrod 262 thus together comprise a lost motion mechanism, in that a portion of the movement of the handle rack does not produce any movement of the pushrod 262. In addition, the handle rack 160, the pushrod 262, and the bracket 268 together comprise a jaw linkage that operably couples the second handle 52 and the second jaw 250. In other words, the handle rack 160, the pushrod 262, and the bracket 268 together provide a mechanical pathway, when the rounded first end 264 of the pushrod contacts the second end 164 of the handle rack, to transmit movement of the second handle 52 to the second jaw 250 such that movement of the second handle 52 effects or produces clamping movement of the second jaw, as explained in more detail below.

The second stapler connecting rod 228 includes a first end portion 236 adjacent its first end 230, which is best shown in FIG. 9. The first end portion 236 of the second stapler connecting rod 228 is coupled to the first handle 32 such that pivotal movement of the first handle causes axial movement of the second connecting rod. More particularly, the first end portion 236 includes, on a downwardly presented surface, as viewed in the FIG. 9, a plurality of teeth 238 and a recess 288. The plurality of teeth 238 are arranged such that the teeth and the first end portion 236 of the second stapler connecting rod 228 are, in effect, a rack. The teeth 238 of the first end portion 236 of the second stapler connecting rod 228 engage a pinion gear assembly 240.

The pinion gear assembly 240 includes a first pinion gear 242 and a coaxial second pinion gear 246, which both rotate about a common axis of rotation 249. The first pinion gear 242 is circular in shape and has a first diameter. The second pinion gear 246 is also circular in shape and has a second diameter that is smaller than the first diameter. A plurality of teeth 244 extend all around the outer periphery of the first pinion gear 242. A plurality of teeth 248 extend all around the outer periphery of the second pinion gear 246. The teeth 244 on the first pinion gear 242 are configured and dimensioned to engage and mate with the teeth 238 on the first end portion 236 of the second stapler connecting rod 228 so that rotational movement of the first pinion gear causes axial movement of the second connecting rod. Together, the first end portion 236 of the second stapler connecting rod 228 and the first pinion gear 242 constitute a rack and pinion assembly. The teeth 248 on the second pinion gear 246 are configured and dimensioned to engage and mate with teeth 302 on a rack 290. Together, the rack 290 and the second pinion gear 246 also constitute a rack and pinion assembly.

The rack 290 has an elongated shape with a first end 292 and a second end 294. A first end portion 296 of the rack 290 adjacent the first end 292 of the rack 290 includes a plurality of teeth 298 that are configured to engage and mate with teeth 38 on the first end portion 34 of the first handle 32. The teeth 38 and the first end portion 34 of the first handle 32 are formed as a sector gear. The teeth 298 on the first end portion 296 of the rack 290 and the teeth 38 on the first end portion 34 of the first handle 32 are configured such that pivotal movement of the first handle about the axis 50 causes axial movement of the rack 290 relative to the housing 24 and the pinion gear assembly 240. A second end portion 300 of the rack 290 adjacent the second end 294 of the rack includes the teeth 302, which are configured to engage and mate with the teeth 248 on the second pinion gear 246. Consequently, as pivotal movement of the first handle 32 causes axial movement of the rack 290, the axial movement of the rack causes rotational movement of the second pinion gear 246 of the pinion gear assembly 240. Rotation of the second pinion gear 246, in turn, causes rotation of the first pinion gear 242 and axial movement of the second stapler connecting rod 228.

Together, the first stapler connecting rods 220, the second stapler connecting rod 228, the pinion gear assembly 240, and the rack 290 comprise a stapler linkage that operably couples the first handle 32 and the first jaw 188. In other words, the first stapler connecting rods 220, the second stapler connecting rod 228, the pinion gear assembly 240, and the rack 290 together provide a mechanical pathway to transmit movement of the first handle 32 to the first jaw 188 such that movement of the first handle 32 effects or produces delivery of a staple (not shown) to tissue disposed adjacent the staple cartridge 192 of the first jaw 188, as explained in more detail below. In this regard, while the first and second stapler connecting rods 220 and 228 are connected to and move with each other, the second stapler connecting rod 228 is engaged with and moves with the pinion gear assembly 240, and the pinion gear assembly 240 is engaged with and moves with the first handle 32, the first stapler connecting rods 220 are simply received in and slide in the channels 210 of the staple cartridge 192 of the first jaw 188. The second ends 224 of the first stapler connecting rods 220 can be slid out the channels 210 in order to facilitate removing and replacing the staple cartridge 192. Nonetheless, movement of the second ends 224 of the first stapler connecting rods 220 and, as explained in more detail below, resultant movement of the staple deployment members (not shown) deploys or forces the staples downward out of the staple cartridge 192 of the first jaw 188 toward the second jaw 250. The first handle 32 is thus operably coupled with the first jaw 188.

A projection 304 extends from the first end portion 296 of the rack 290 adjacent the teeth 298. The projection 304 extends farther from the rack 290 than the teeth 298 and is configured to engage and slide along an arcuate surface 40 of the first handle 32. The first end portion 296 of the rack 290 is positioned within the housing 24 such that the first end portion extends between the guide members 184 on the handle rack 160. Together, the projection 304 on the rack 290 and the guide members 184 on the handle rack 160 help to restrain or limit movement of the rack 290 in a vertical direction, as viewed in FIG. 9, and to maintain the rack 290 in a horizontal plane so that the teeth 302 on the second end portion 300 of the rack maintain engagement with the teeth 248 on the second pinion gear 246 and the teeth 298 on the first end portion 296 of the rack maintain engagement with the teeth 38 on the first handle 32.

When the stapling device 20 is fully assembled, the clamp members 70 are positioned on opposite sides of the stapler 186 and the longitudinal axis 68, as shown in FIGS. 1 and 2. The clamp members 70 are disposed in approximately the same position along the longitudinal axis 68 as the first and second jaws 188 and 250 or are disposed slightly rightward of the left ends of the first and second jaws, as viewed in FIGS. 1 and 2. The clamp members 70 do not project forward (to the left in FIGS. 1 and 2) of the first and second jaws 188 and 250. The clamp members 70 also present their respective clamping surfaces in the same orientation as the jaws 188 and 250. Specifically, the jaws 188 and 250 move toward and away from each other in generally vertical directions, as viewed in FIGS. 1 and 2. The second end portions 88 of the second links 82 of the clamp members 70 and the second end portions 106 of the third links 100 of the clamp members similarly move toward and away from each other in generally vertical directions, as viewed in FIGS. 1 and 2. In effect, the jaws 188 and 250 open and close in the same directions as the clamp members 70. When the operator pulls the second handle 52, the clamp members 70 grasp and pull tissue into the space between the first and second jaws 188 and 250 of the stapler 186. After a predetermined delay, as explained more fully below, the first and second jaws 188 and 250 begin to close until the pulled tissue is securely within the clamp members 70 and the jaws. Subsequent pulling of the first handle 32 causes a staple within the staple cartridge 192 of the first jaw 188 to be driven through the tissue. The staple is bent by the second jaw 250 until the tissue is securely stapled together. The second handle 52 can then be released to release the now stapled tissue.

Figure 11:
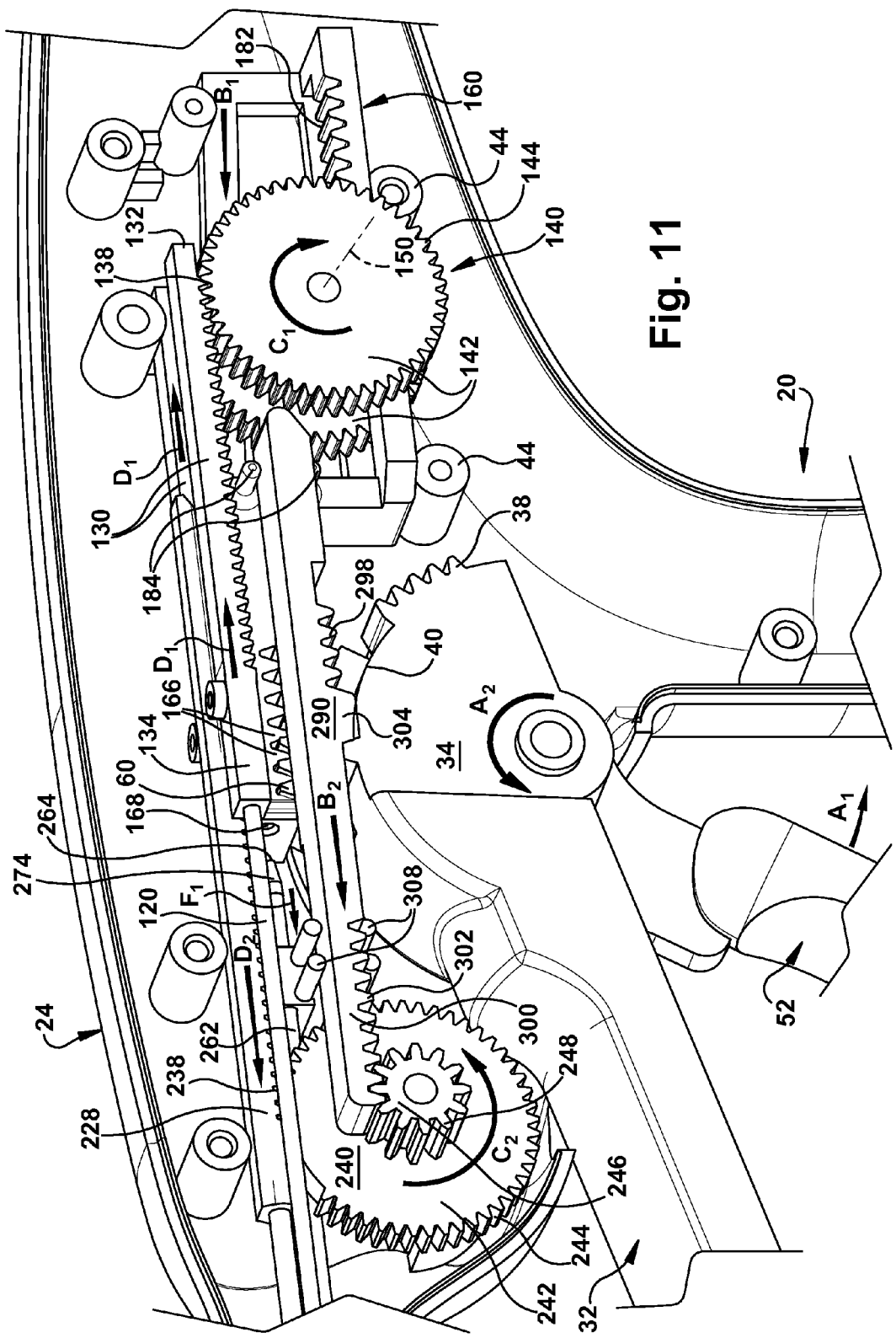
FIG. 11 an enlarged view of the stapler of FIG. 1.
Figure 12:
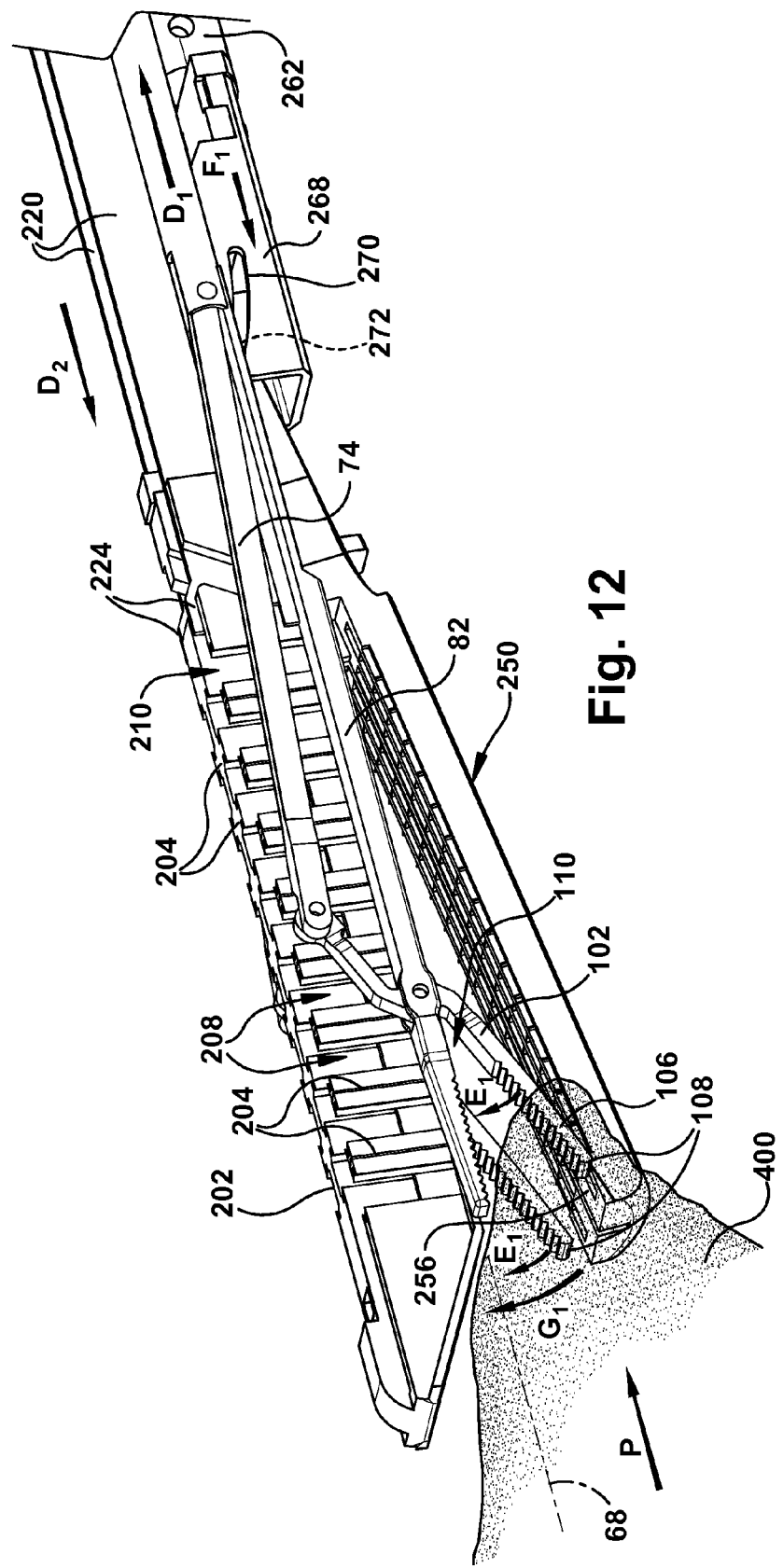
FIG. 12 is an enlarged view of a portion of the stapler of FIG. 1.

Operation of the stapling device 20 is shown in more detail in FIGS. 11-12. In use, the stapling device 20 is endoscopically brought into proximity with tissue 400 that is desired to be stapled together. The portions of the clamp members 70 and the stapler 186 that extend axially beyond the second end 66 of the tubular member 62 may be covered with a releasable gelatin capsule (not shown) or a movable sheath (not shown) to protect the stapler until the endoscope reaches the desired position within the patient.

The tissue 400 is positioned within the spaces 110 between the teeth 90 on the second ends 86 of the second links 82 and the teeth 108 on the second ends 104 of the third links 100 using conventional visualization techniques. The second handle 52 is then pivoted counterclockwise in the direction $A_1$, causing the teeth 60 on the first end portion 54 of the second handle to move the teeth 166 on the first arm 170 of the handle rack 160, and thus the entire handle rack, in the direction $B_1$, which is to the left in FIG. 11. Axial movement of the handle rack 160 in the direction $B_1$ causes the teeth 182 on the third arm 174 of the handle rack 160 to impart rotation, via the teeth 148, to the second pinion gear 146 of the pinion gear assembly 140 in clockwise direction $C_1$ about the axis 150 and relative to the housing 24. Since the second pinion gear 146 and the first pinion gears 142 are interconnected for joint rotation together, the first pinion gears 142 likewise rotate in the clockwise direction $C_1$. The teeth 144 of the rotating first pinion gears 142 cause axial movement of the teeth 138 on the portion 136 of each rack 130 in the direction $D_1$, which is to the right in FIG. 11, and, thus, axial movement of both racks in the direction $D_1$.

Since the clamp connecting rods 120 are fixed to the second ends 134 of the racks 130, movement of the racks 130 to the right in FIG. 11, which is in the direction $D_1$, causes the first connecting rods likewise to move axially to the right in the direction $D_1$ (see also FIG. 3). Axial movement of the clamp connecting rods 120 in the direction $D_1$ pulls the first links 74 of the clamp members 70 in the direction $D_1$ relative to the second links 82, thereby causing clockwise pivotal movement of the third links 100 relative to the second links as indicated by arrows $E_1$ and reducing the size of the spaces 110 between the second links and the third links. Because the tissue 400 is positioned within the spaces 110 between the second links 82 and the third links 100, rotation of the third links in the direction $E_1$ causes the atraumatic teeth 90 and 108 of the second and third links, respectively, to clamp down upon the tissue. When this occurs, the first links 74 are prevented from moving relative to the second links 82.

As the first, second, and third links 74, 82, 100 are all connected to one another, when the first link is thereafter pulled in the direction $D_1$ by the clamp connecting rods 120, the second and third links are also pulled in the direction $D_1$. In other words, subsequent axial movement of the clamp connecting rods 120 in the direction $D_1$ causes the atraumatic teeth 90 and 108 of the second and third links 82 and 100, respectively, to clamp down upon the tissue as the tissue is simultaneously pulled in the direction P, which is to the right in FIG. 12, by the moving first, second, and third links 74, 82, and 100, respectively. The simultaneous clamping and pulling of the tissue 400 by the stapler 186 draws in and maintains the tissue between the first jaw 188 and the second jaw 250 of the stapler 186.

Along with reducing the size of the spaces 110 between the second links 82 and the third links 100 and pulling the first, second, and third links 74, 82, and 100, axial movement of the handle rack 160 to the left in FIGS. 11 and 12 in the direction $B_1$ also causes the handle rack to move into engagement with the rounded first end 264 of the pushrod 262 (FIG. 11). Continued axial movement of the handle rack 160 in the direction B1 causes the pushrod 262 to move to the left in FIGS. 11 and 12 in the axial direction F1 (FIG. 12). When the pushrod 262 moves in the direction F1, the second end 266 of the pushrod 262 moves towards the second jaw 250, causing the pins 272 of the second jaw to slide along the slots 270 in the bracket 268 attached to the pushrod and pivot the second jaw upward and toward the first jaw 188 in the direction $G_1$. Rotation of the second handle 52 in the direction $A_1$ therefore results in the tissue 400 being grasped by the first and second jaws 188 and 250, respectively, after initially being grasped and pulled between the jaws by the clamp members 70.

As the handle rack 160 is initially displaced as far as it can be to the right, as viewed in FIG. 11, the rounded first end 264 of the pushrod 262 is initially spaced from the recess 168 in handle rack 160 by the distance "d". Consequently, there is a delay between the commencement or start of movement of the handle rack 160 in the direction $B_1$ and the commencement or start of the pivoting of the second jaw 250 towards the first jaw 188. This time delay or delayed response ensures that the first, second, and third links 74, 82, and 100, respectively, have begun grasping and pulling the tissue 400 into the space between the first jaw 188 and the second jaw 250 prior to the second jaw pivoting upwards towards the first jaw. Ultimately, however, the tissue 400 is grasped and pulled into the space between the first and second jaws 188 and 250 by the first, second, and third links 74, 82, and 100 and further clamped by the first and second jaws.

Once the tissue 400 is positioned between the first jaw 188 and the second jaw 250, the user may further manipulate the stapling device 20 to suture the tissue. In particular, the user may pull the first handle 32 to rotate the first handle in a counter-clockwise direction $A_2$ relative to the housing 24 as shown in FIGS. 10-11. Rotation of the first handle 32 in the direction $A_2$ causes the projection 304 on the rack 290 to slide along the arcuate surface 40 of the first handle until the teeth 38 on the first handle engage the teeth 298 on the rack. Continued rotation of the first handle 32 in the counter-clockwise direction $A_2$ causes axial movement of the rack 290 in the direction $B_2$ due to the mating engagement of the teeth 38 and 298.

Movement of the rack 290 in the direction $B_2$ is guided by the guide members 184 on the handle rack 160, by a plurality of projections 308 formed on the inside of one half 24b of the housing 24, and the arcuate surface 40 of the first handle 32. Due to the toothed engagement between the teeth 302 on the second end portion 300 of the rack 290 and the teeth 248 on the second pinion gear 246 of the pinion gear assembly 240, as the rack moves in the direction $B_2$, the second pinion gear and, thus, the entire pinion gear assembly is rotated in a counterclockwise direction $C_2$. As the pinion gear assembly 240 and, thus, the teeth 244 on the first pinion gear 242 of the pinion gear assembly rotate in the counter-clockwise direction $C_2$, the engagement between the teeth 244 and the teeth 238 on the second stapler connecting rod 228 causes the second stapler connecting rod to move in the direction $D_2$, which is to the left in FIG. 11.

The fixed connection between the first and second stapler connecting rods 220 and 228 causes the first connecting rods to move in the direction $D_2$ (FIG. 12). This causes the second ends 224 of the first stapler connecting rods 220 advance through the channels 210 in the staple cartridge 192 (FIG. 8A) and also causes the sharpened projection 226 on the second end 224 of the optional first stapler connecting rod 220, if present, to advance through the central slot 200 in the staple cartridge 192 (FIG. 8B). When the second ends 224 of the first stapler connecting rods 220 move through the channels 210 in the staple cartridge 192 in this manner, the second ends 224 contact and push on corresponding staple deployment members (not shown). The staple deployment members (not shown) may be components of the staple cartridge 192. As the staple deployment members (not shown) are moved to the left, as viewed in FIG. 12, the staple deployment members engage individual staples and deploy or force the staples downward out of the staple cartridge 192 toward the second jaw 250. As each staple (not shown) positioned within an opening 208 of the staple cartridge 192 is forced out of the staple cartridge, the ends of the staple are forced into engagement with the staple bending structure 256 on the second jaw 250.

Since the tissue 400 is positioned between the first and second jaws 188 and 250, the staples are forced through the tissue and into engagement with the second jaw. The staple bending structure 256 on the second jaw 250 bends the staple adequately to secure the staple to the tissue 400 and, thus, secure portions of the tissue to one another. By grasping and pulling the tissue 400 into a position between the first and second jaws 188 and 250 before applying the staple to the tissue, a greater surface area of the tissue can be stapled together.

To release the stapled tissue 400 from the stapling device 20, the second handle 52 is pivoted away from the grip assembly 22, i.e., in a clockwise direction opposite to the direction $A_1$. This rotation causes the handle rack 160 to move to the right, as viewed in FIG. 11, in a direction opposite to the direction $B_1$, which causes the pinion gear assembly 140 to rotate counter-clockwise about the axis 150, in a direction opposite the direction $C_1$. Counter-clockwise rotation of the pinion gear assembly 140 causes the rack 130 and, thus, the first link 74 to move to the left, as viewed in FIG. 12, in a direction opposite to the direction $D_1$ and release the teeth 90 and 108 from the stapled tissue 400. Movement of the handle rack 160, the pinion gear assembly 140, the rack 130 and/or the links 74, 82, 100 in this manner may be aided by a biasing spring (not shown).

Movement of the second handle 52 in the direction opposite to the direction $A_1$ also moves the handle rack 160 out of engagement with the rounded first end 264 of the pushrod 262. The separation between the second end 164 of the handle rack 160 and the rounded first end 264 of the pushrod 262 permits the pushrod to move to the right, as viewed in FIG. 12, in a direction opposite to the direction $F_1$ under bias from a spring (not shown), thereby releasing the first and second jaws 188 and 250 from the stapled tissue 400.

From the above description of the invention, those skilled in the art will perceive improvements, changes and modifications. For example, the clamp members 70 of the present invention have been illustrated in combination with a particular stapler 186. In particular, the stapler 186 is shown as one designed to use a staple cartridge 192 of a type sold by Ethicon Endo-Surgery, Inc. of Somerville, N.J. The clamp members 70 could be used, however, with other stapler designs or mechanisms. In addition, the clamp members 70 could be added as separate components to a pre-existing stapler. Further, although the present invention has been described for use in treating Zenker's Diverticulum, those having ordinary skill will appreciate that the stapling device of the present invention can be sized and shaped to endoscopically staple tissue in any clinical application, e.g., bariatrics, cardiac care, or any place within a patient where it is desirable to staple tissue. Such improvements, changes and modifications within the skill of the art are intended to be covered by the appended claims.

Having described the invention, the following is claimed:

1. An endoscopic stapler for suturing tissue comprising:
    a first jaw and a second jaw, the first jaw including structure for retaining a plurality of staples, the first jaw and second jaw being mounted to permit pivotal movement of the first and second jaws relative to one another;
    at least one clamp member for clamping tissue and pulling the tissue into a position between the first jaw and the second jaw to facilitate inserting at least one staple of the plurality of staples into the tissue;
    a first handle operably coupled with the first jaw such that movement of the first handle effects delivery of the at least one staple of the plurality of staples to the tissue;
    a second handle operably coupled with the second jaw and the at least one clamp member such that movement of the second handle effects movement of the second jaw and movement of the at least one clamp member;
    a stapler linkage coupling the first handle and the first jaw;
    a clamp linkage coupling the second handle and the at least one clamp member; and
    a jaw linkage coupling the second handle and the second jaw so as to permit both movement of the second handle and the second jaw relative to one another and movement of the second handle and the second jaw together with one another.

2. An endoscopic stapler according to claim 1 wherein the clamp linkage includes a rack and pinion assembly.

3. An endoscopic stapler according to claim 1 wherein the at least one clamping member comprises two clamp members and wherein the clamp linkage couples the second handle and both clamp members.

4. An endoscopic stapler according to claim 1 wherein the clamp linkage is connected to the jaw linkage such that movement of the second handle causes movement of the clamp linkage and movement of at least a part of the jaw linkage.

5. An endoscopic stapler according to claim 4 wherein at least one portion of the clamp linkage is also a portion of the jaw linkage.

6. An endoscopic stapler according to claim 1 wherein the jaw linkage includes a lost motion mechanism.

7. An endoscopic stapler according to claim 1 wherein the jaw linkage includes first and second members mounted for both movement relative to one another and movement together with one another.

8. An endoscopic stapler according to claim 1 wherein the stapler linkage includes a rack and pinion assembly.

9. An endoscopic stapler according to claim 1 wherein the second jaw is mounted to pivot relative to the first jaw.

10. An endoscopic stapler according to claim 1 wherein the at least one clamp member comprises two clamp members, the two clamp members being laterally spaced from one another, the first and second jaws being disposed laterally between the two clamp members.

11. An endoscopic stapler according to claim 1 wherein the second handle is operably coupled with the at least one clamp member such that movement of the second handle effects movement of the at least one clamp member both to clamp the tissue and also to pull the tissue into the position between the first jaw and the second jaw.

12. An endoscopic stapler according to claim 11 wherein the second handle is operably coupled with the second jaw such that (a) the second handle moves relative to the second jaw as movement of the second handle effects movement of the at least one clamp member both to clamp the tissue and also to pull the tissue into the position between the first jaw and the second jaw and (b) the second handle thereafter moves together with the second jaw as movement of the second handle effects movement of the second jaw toward the first jaw.

13. An endoscopic stapler for suturing tissue comprising:
    a first jaw and a second jaw, the first jaw including structure for retaining a plurality of staples, the first jaw and second jaw being mounted to permit pivotal movement of the first and second jaws relative to one another;
    two clamp members for clamping tissue and pulling the tissue into a position between the first jaw and the second jaw to facilitate inserting at least one staple of the plurality of staples into the tissue, the two clamp members being laterally spaced from one another, the first and second jaws being disposed laterally between the two clamp members;
    a handle operably coupled with the second jaw and with the clamp members such that movement of the handle effects pivotal movement of the second jaw relative to the first jaw and also effects clamping movement of the clamp members;
    a clamp linkage coupling the handle and the clamp members; and
    a jaw linkage coupling the handle and the second jaw so as to permit both movement of the handle and the second jaw relative to one another and movement of the handle and the second jaw together with one another.

14. An endoscopic stapler according to claim 13 wherein the handle is operably coupled with the clamp members such that movement of the handle effects movement of the clamp members both to clamp the tissue and also to pull the tissue into the position between the first jaw and the second jaw.

15. An endoscopic stapler according to claim 14 wherein the handle is operably coupled with the second jaw such that (a) the handle moves relative to the second jaw as movement of the handle effects movement of the clamp members both to clamp the tissue and also to pull the tissue into the position between the first jaw and the second jaw and (b) the handle thereafter moves together with the second jaw as movement of the handle effects movement of the second jaw toward the first jaw.

\* \* \* \* \*